United States Patent
Schouenborg (12) 
(10) Patent No.: US 6,504,603 B1
(45) Date of Patent: Jan. 7, 2003

(54) METHOD AND DEVICE FOR DETECTING UNDESIRED MATTER IN EGGS

(75) Inventor: Kurt Otto Peter Schouenborg, Roedovre (DK)

(73) Assignee: FPS Food Processing Systems B. V. (NL)

(*) Notice: Subject to any disclaimer, the term of this patent is extended or adjusted under 35 U.S.C. 154(b) by 0 days.

(21) Appl. No.: 09/462,062
(22) PCT Filed: Jul. 2, 1998
(86) PCT No.: PCT/NL98/00380
§ 371 (c)(1), (2), (4) Date: Feb. 11, 2000
(87) PCT Pub. No.: WO99/01762
PCT Pub. Date: Jan. 14, 1999

(30) Foreign Application Priority Data

Jul. 3, 1997 (NL) .............................................. 1006460

(51) Int. Cl.⁷ ............................................... A01K 43/00
(52) U.S. Cl. ......................................... 356/53; 209/511
(58) Field of Search .............................. 356/53; 209/511

(56) References Cited

U.S. PATENT DOCUMENTS

| | | | | |
|---|---|---|---|---|
| 2,823,800 A | * | 2/1958 | Bliss | 356/53 |
| 3,004,664 A | * | 10/1961 | Dreyfus | 356/53 |
| 4,039,259 A | * | 8/1977 | Saito et al. | 356/53 |
| 4,063,822 A | * | 12/1977 | Dejong et al. | 356/53 |
| 4,182,571 A | * | 1/1980 | Furuta et al. | 356/53 |

* cited by examiner

*Primary Examiner*—Richard A. Rosenberger
(74) *Attorney, Agent, or Firm*—Larson & Taylor, PLC (57) ABSTRACT

Described is a method for determining whether a brown egg contains undesired matter such as blood. In two wavelength ranges the transmission of the egg is examined, one of those wavelength ranges corresponding to an absorption peak of blood. The transmission signal of the other wavelength range is corrected with a fixed fraction γ to correct for the egg being brown.

26 Claims, 5 Drawing Sheets

METHOD AND DEVICE FOR DETECTING UNDESIRED MATTER IN EGGS

This invention relates to a method for detecting the presence of undesired matter in an egg as described in the preamble of claim 1. Such a method is generally known in practice and is based on the principle of color spectrum photometry. Although the present invention is generally applicable for detecting undesired matter in general, the present invention is of interest in particular for detecting the presence of blood in eggs, for which reason the present invention will be described hereinbelow for such an exemplary application.

In practice, it may happen that an egg intended for consumption, for instance a chicken egg, contains blood. Although the presence of blood is, in principle, harmless, the consumer generally does not find the presence of blood a pleasant sight. For this reason, egg-processing companies generally entertain the desire to supply "pure" eggs only, that is, eggs with as little undesired matter, such as blood, as possible. This implies there is a need for detection equipment to determine whether blood is present in an egg. Such detection equipment is coupled to sorting equipment to remove, during the sorting and packing of eggs, the unsuitable eggs, that is, the eggs that contain undesired matter such as blood.

Naturally, such detection equipment should be non-destructive. A well-proven detection method for detecting the presence of blood relies on the fact that an egg is semi-transparent, and is based on the absorption characteristics of eggs and blood. Blood has a strong absorption line at 577 nm; a normal egg has a much lower absorption at this wavelength, and the absorption characteristic of a normal egg is virtually flat in this wavelength range. By directing light at an egg and measuring the amount of transmitted light at 577 nm, the presence of blood can in principle be determined. However, the light, when passing through the egg, will be considerably weakened by the egg itself, and the extent of weakening can vary from one egg to another: it depends inter alia on the thickness of the egg. To correct for the extent of absorption/weakening by the egg itself, the amount of transmitted light is also measured in a narrow wavelength band at some distance from the absorption line referred to; in practice, a wavelength distance of 20 nm is used, and this reference measurement is carried out at approximately 597 nm. The result of the measurement at 577 nm can be corrected for the result of the measurement at 597 nm, to thereby obtain a measuring signal that depends substantially exclusively on the absorption by blood.

In practice, this method has proven to yield good results. Even eggs that contain only minute amounts of blood can be detected with a high probability, while the probability that a bloodless egg is falsely rejected is particularly low.

The good results referred to, however, have so far applied to white eggs only. In colored eggs, the results are less good, because the coloring of the shell plays a role. In particular, the measuring method referred to has been found to be less reliable in brown eggs. The reason for this reduced reliability has been found to reside in the fact that the shell of brown eggs itself exhibits an absorption in the range of 577 nm. This makes it difficult to discriminate between absorption caused by blood and absorption caused by the brown shell.

It is therefore an object of the present invention to make the known blood detection method suitable for examining brown eggs as well.

In particular, the object of the present invention is to provide a relatively simple method which enables determining the presence of blood in brown eggs with great accuracy.

More particularly, the object of the present invention is to provide a method for processing the measuring signals that are provided by a standard detection device, without requiring modification of such a standard detection device.

To that end, the method according to the invention has the features as described in the characterizing clause of claim 1.

These and other aspects, features and advantages of the present invention will be clarified by the following description of a preferred embodiment of a method and device according to the invention, with reference to the drawing, in which.

Figure 1:
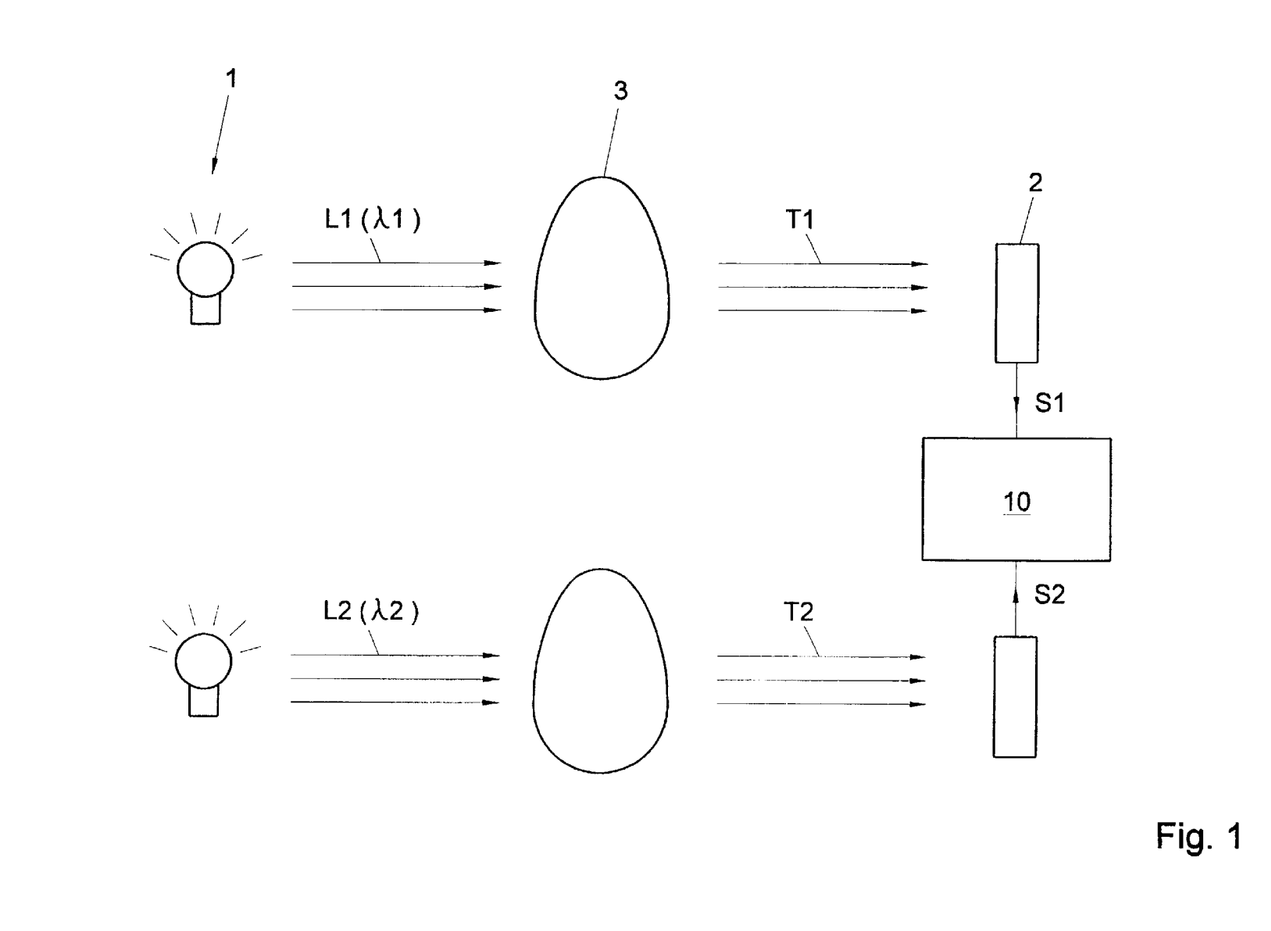
FIG. 1 schematically illustrates the principle of blood detection in eggs.

FIG. 1 illustrates the principle of blood detection in eggs, which is known per se. An egg 3 to be examined is subjected to a first light radiation L1 having a first predetermined wavelength $\lambda 1$, coming from a light source 1, and the radiation T1 transmitted by the egg 3 at this wavelength is received by a detector 2, which provides a first electrical signal S1 which is representative of the intensity of the received first transmission radiation T1. Similarly, a second electrical signal S2 is provided, which is representative of the received second transmission radiation T2 at a second predetermined wavelength $\lambda 2$. These two signals S1 and S2 are presented to a signal processing device 10, which on the basis of those signals decides whether or not the egg 3 under examination contains blood. In practice, the wavelengths used are approximately 597 nm ($\lambda 1$) and 577 nm ($\lambda 2$), but other wavelengths are, in general, also conceivable.

In FIG. 1, for the sake of clarity, the light source 1, the egg 3, and the detector 2 are depicted twice. It is indeed possible to use two different light sources, each transmitting only one of the wavelengths mentioned, and to use two different light sources, each providing only one of the electrical signals mentioned. It is also possible, however, that the two electrical signals S1 and S2 are provided by one and the same detector 2, which is sensitive to at least both wavelengths $\lambda 1$ and $\lambda 2$. Also, the light Li and the light L2 can originate from one and the same light source 1, which generates light containing at least both wavelengths $\lambda 1$ and $\lambda 2$. To obtain the first electrical signal S1, a first filter (not shown for the sake of simplicity) can be placed in the light path, either between the light source 1 and the egg 3, or between the egg 3 and the detector 2, which first filter is designed to transmit substantially exclusively the first wavelength $\lambda 1$. Similarly, the second electrical signal S2 can be obtained by making use of a second filter, which is designed to transmit substantially exclusively the second wavelength $\lambda 2$.

Naturally, other measuring arrangements are also possible, as will be clear to one skilled in the art. In a particular embodiment, light containing both wavelengths $\lambda 1$ and $\lambda 2$ is aimed at the egg 3 and after passing through the egg 3 is received by a detector with two detection channels which are sensitive to the respective wavelengths.

Generally, it holds that the combination of the signals S1 and S2 is representative of the absorption characteristic of the egg 3 in the range 577–597 nm. If the intensity of the light L1 and L2 emitted by the light source is denoted I(L1) and I(L2), respectively, and the absorption coefficient of an egg at the wavelengths $\lambda 1$ and $\lambda 2$ is denoted $\alpha 1$ and $\alpha 2$, respectively, the magnitude of the electrical detector signals S1 and S2 can be written as $f1 \cdot (1-\alpha 1) \cdot I(L1)$ and $f2 \cdot (1-\alpha 2) \cdot I(L2)$, where f1 and f2 are proportionality factors expressing inter alia the sensitivity of the detector to the wavelengths $\lambda 1$ and $\lambda 2$. The above-mentioned combination of the signals S1 and S2 can be expressed, for instance, by defining a state parameter M which is a function of a combination of S1 and S2, for instance M=S1/S2 or M=S1−S2. Hereinafter, the invention will be further elaborated under the assumption that the state parameter is defined on the basis of a differential signal between the detector signals; it will be clear to one skilled in the art how the present invention can be implemented on the basis of a coefficient signal.

For an egg without blood, the transmission characteristics (and absorption characteristics) at the two wavelengths $\lambda 1$ and $\lambda 2$ are virtually identical to each other, and any differences in those characteristics will be virtually the same for different eggs with respect to each other. Although the values of S1 and S2 can vary for individual eggs, for instance depending on the size of the eggs, the foregoing means that the state parameter M=S1−S2 for bloodless white eggs will be substantially equal to zero or will, at most, have a small value which will, in principle, be the same for all bloodless white eggs. This value will be designated hereinafter as reference state value $M_{white,0}$.

Because blood has a narrow absorption peak at approximately 577 nm, with a peak width of approximately 10 nm, it holds for a white egg containing blood that the second absorption coefficient $\alpha 2$ will be considerably greater than if the egg did not contain any blood, while for the first absorption coefficient al the presence or absence of blood will make little difference, if any. This means that the absolute value of the state parameter M will then be significantly greater than the above-mentioned "reference state value" $M_{white,0}$. In white eggs, this is a reliable indication of the presence of blood, and the magnitude of the difference $M-M_{white,0}$ is a reliable measure of the amount of blood in the egg in question. To determine whether the amount of blood in an egg is acceptable or not, a state threshold $\Delta M$ can be defined, and $M-M_{white,0}$ can be compared with this predefined state threshold $\Delta M$; if $M-M_{white,0}<\Delta M$, the amount of blood is acceptable.

As for an egg with a brown shell, the matter is more complicated, because the brown shell also has an absorption peak at $\lambda 2$. Then the mere given that the state parameter M is significantly greater than the above-mentioned reference state value $M_{white,0}$ is not a reliable indication of the presence of blood. The present invention provides a solution to this problem, which will be described in the following.

Figure 2:
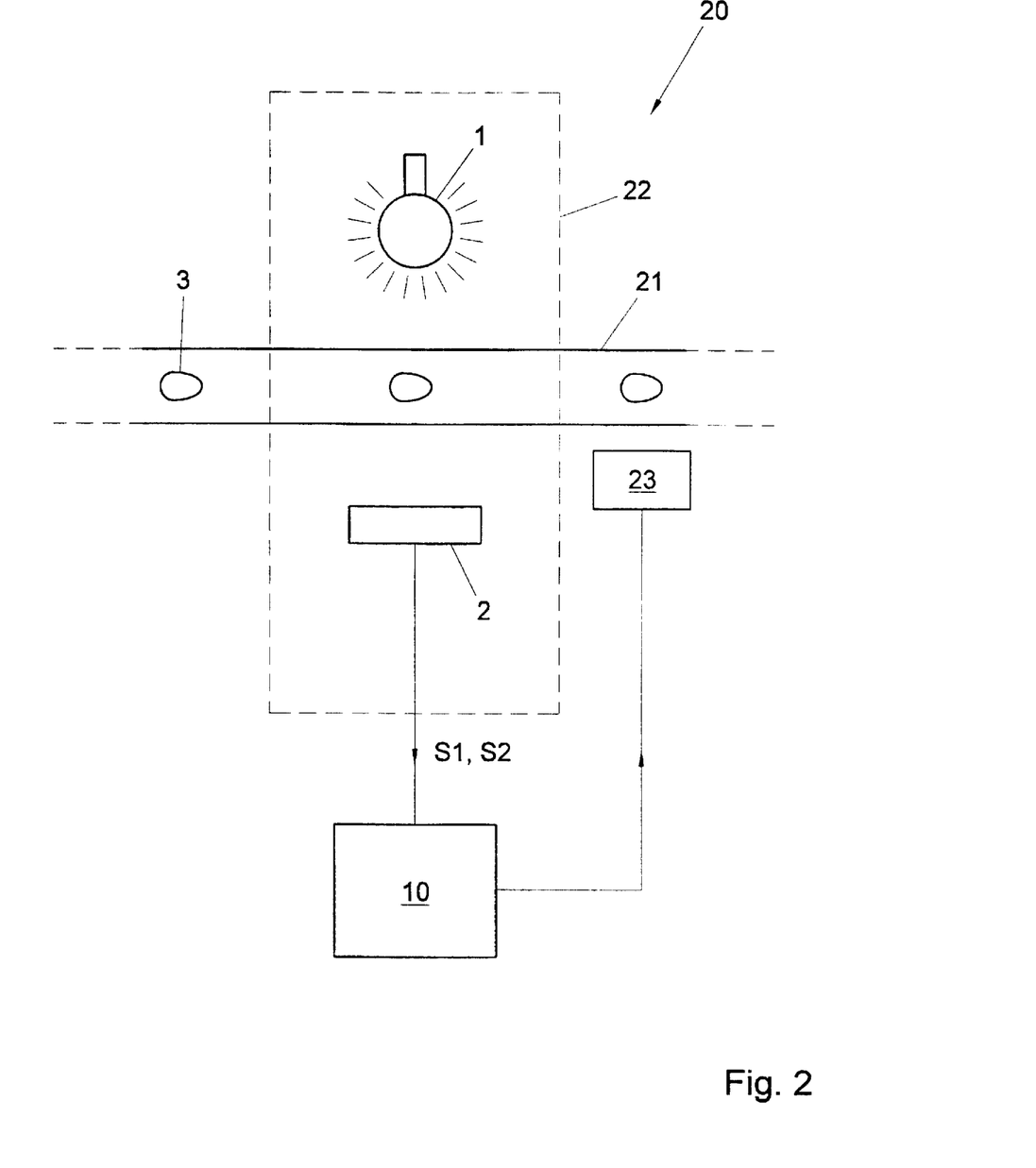
FIG. 2 schematically shows a blood detection device.

FIG. 2 diagrammatically shows a blood detection device 20. It comprises a conveying device 21 for eggs 3, for instance a conveyor or the like. Arranged along the conveying device 21 is a detection station 22, which comprises, for instance, a light source 1 and a detector 2, as illustrated in more detail in FIG. 1. The blood detection device 20 further comprises a signal processing device 10 which receives the signals S1 and S2 from the detector 2. Further, a removal device 23 is provided, which is arranged to remove eggs from the conveying device 21 under the control of the signal processing device 10.

In the foregoing, it has been mentioned that the reference state value $M_{white,0}$ is very small. To eliminate any instrumentation differences, it is preferably ensured that $M_{white,0}$ is substantially equal to zero. To that end, the blood detection device 20 is adjusted in a white-calibration procedure, such that in bloodless white eggs the two signals S1 and S2 are substantially equal to each other; in other words, $M_{white,0}$ is made equal to zero. This can be accomplished in various ways. Firstly, it is possible to set the light strength of the light source 1 for generating L1 and/or the light strength of the light source 1 for generating L2, such that upon detection it is found that S1=S2. Secondly, it is possible, for instance, to multiply in the signal processing device 10 one of the received signals S1, S2 by a first correction factor c, such that $c \cdot S1=S2$ and $S1=c \cdot S2$, respectively.

Hereinafter, it will be assumed that in the calibration the signal processing device 10 multiplies the first detector signal S1 by the first correction factor c, such that $c \cdot S1=S2$. It is noted that this correction can be carried out through hardware, by an amplifier with an adjustable amplification factor, but it is also possible to carry out this correction through software in the signal processing device 10.

Figure 3A:
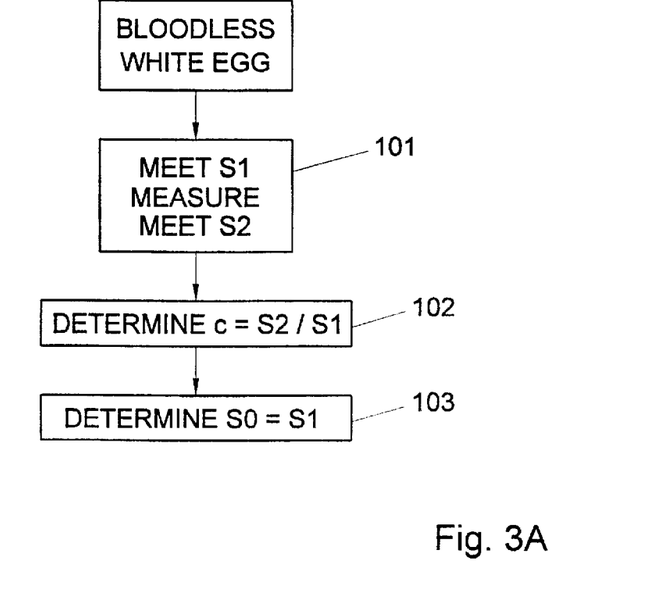
FIG. 3A is a flow diagram illustrating a white-calibration procedure.

The above-mentioned white-calibration procedure is illustrated in FIG. 3A. A bloodless white egg is subjected to the radiation L1 and L2, and the signals S1 and S2 are measured (step 101). Then the first correction factor c is determined as c=S2/S1 (step 102). If desired, the steps 101 and 102 can be repeated for several eggs, and the obtained values of c can be averaged.

Figure 4:
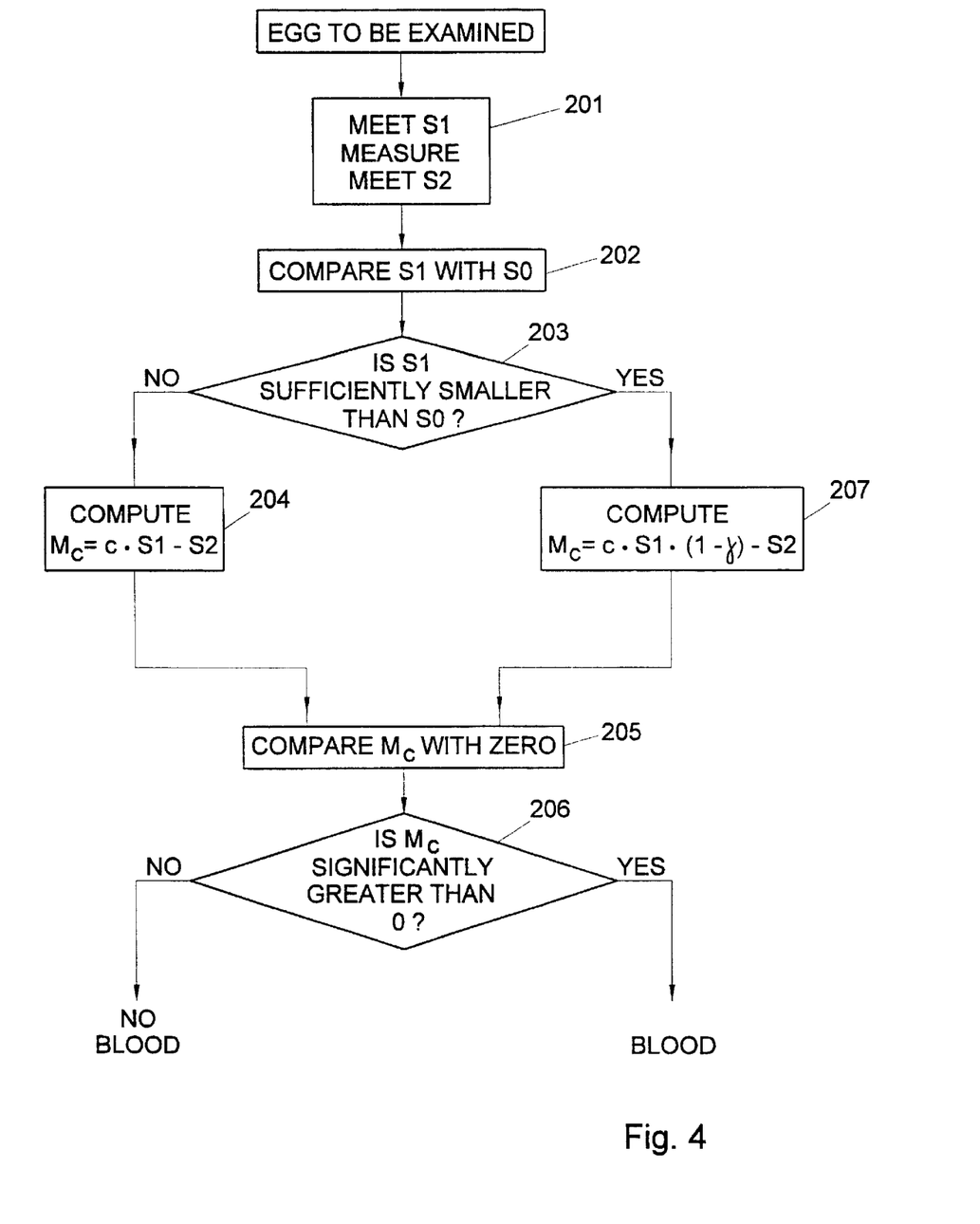
FIG. 4 is a flow diagram illustrating a first example of a measuring procedure according to the present invention.

FIG. 4 illustrates an example of the actual measuring procedure according to the present invention. First, it is determined whether an egg to be examined is a white or a brown egg. This can be accomplished in different ways. Thus, it is possible, for instance, to employ a color-sensitive detector, which is known per se. In a preferred embodiment of the method according to the present invention, however, use is made of the signals S1 and S2 provided by the detectors 2, so that utilization of a separate color-sensitive detector is not needed. The fact is that it has been found that in brown eggs the absorption coefficients $\alpha 1$ and $\alpha 2$ are considerably greater than in white eggs, so that the provided signals S1 and S2 have a considerably smaller intensity, making it possible to discriminate between brown and white eggs on the basis of those signals S1 and S2.

According to the present invention, therefore, in a preferred embodiment of the white-calibration procedure, the magnitude of the signal S1 as obtained from bloodless white eggs is fixed as a reference S0 (step 103, FIG. 3A), which will hereinafter be referred to by the term "white-reference". If desired, step 103 can be repeated for multiple eggs, and the obtained values of S0 can be averaged.

In the actual measuring procedure on an unknown egg (FIG. 4) the signals S1 and S2 are measured (step 201). To determine whether this unknown egg is a white or a brown egg, in a preferred embodiment of the measuring procedure, the measured signal S1 is compared with the above-mentioned white-reference S0 (step 202). If S1 is smaller than S0 to a sufficient extent, for instance S1<75% of S0, it is decided that the egg under examination is a brown egg; if not, it is decided that the egg under examination is a white egg (step 203).

If it has been decided that the egg under examination is a white egg, the measuring signals S1 and S2 are further processed in a conventional manner to detect the presence of blood. In step 204, a corrected state parameter $M_c$ is computed as $M_c=cS1-S2$. In step 205 $M_c$ is compared with zero. If $M_c$ is significantly greater than zero, it is concluded that the egg in question contains blood; if not, it is concluded that the egg in question does not contain any blood (step 206). On the basis of this outcome, the signal processing device 10 can control the removal device 23 to remove the blood-containing egg.

If, however, it is decided that the egg under examination is a brown egg, first a correction is performed on the measuring signals S1 and/or S2 to correct for the shell being brown (step 207). It has been found that such a correction, if desired, can be carried out in the same manner for all brown eggs, regardless of the degree of brownness, shell thickness, etc. The magnitude of the correction has likewise been priorly determined, viz. in a calibration procedure which will be designated as "brown-calibration procedure", utilizing bloodless brown eggs.

Figure 3B:
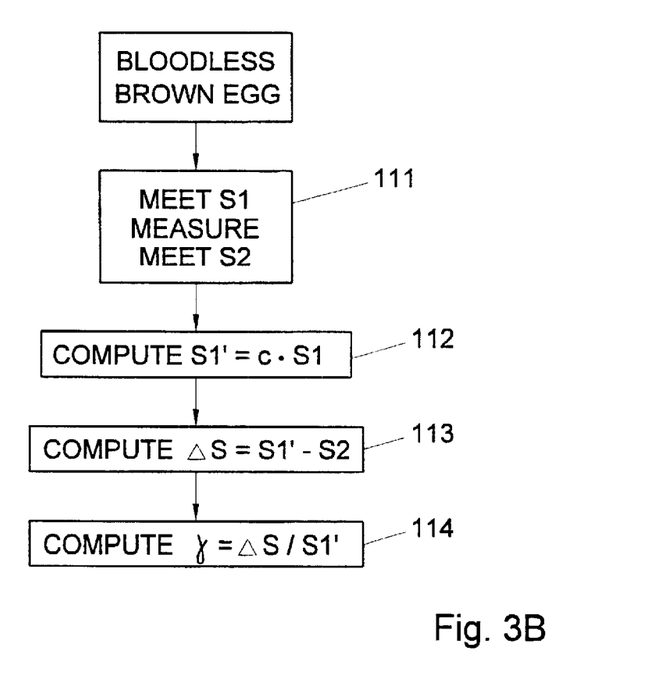
FIG. 3B is a flow diagram illustrating a brown-calibration procedure.

The brown-calibration procedure is illustrated in FIG. 3B. A bloodless brown egg is subjected to the radiation L1 and L2, and the signals S1 and S2 are measured (step 111). Then the signal S1 is corrected with the first correction factor c to provide a corrected signal S1' according to the formula S1'=c·S1 (step 112). As mentioned before, brown eggs exhibit an absorption at 577 nm, so that for brown eggs S1' will be greater than S2. The differential signal $\Delta S$ is determined according to the formula $\Delta S$=S1'−S2 (step 113). Then this differential signal $\Delta S$ is expressed as a fraction of the corrected signal S1', according to the formula $\Delta S$=γ·S1', that is, the fraction γ is computed according to the formula γ=$\Delta S$/S1' (step 114). Alternatively, the steps 112–114 can be combined into a single step in which the fraction y is determined according to the formula γ=(c·S1−S2)/c·S1. If desired, the steps 111–114 can be repeated for multiple eggs, and the obtained values of γ can be averaged.

In the eventual measuring procedure, if in step 203 it has been decided that the egg under examination is a brown egg, the corrected state parameter $M_c$ is computed as $M_c$=(1−γ) c·S1−S2 (step 207). Then, in a comparable manner to that described in respect of white eggs, $M_c$ is compared with zero, that is, the measuring procedure proceeds, after step 207, with step 205 already mentioned. Accordingly, it holds that further the following method step is carried out: (f) only for brown eggs, the first and second measuring signal are corrected relative to each other with a fraction γ. This can be carried out by a correction of the first signal S1 relative to the second signal, a correction of the second signal relative to the first signal, or a correction of the first and second signal whereby the signals are corrected relative to each other. In this example, it holds in particular that an (S1) of the measuring signals is corrected with the fraction γ. Because according to the invention, the measuring signals S1 and S2 must be corrected relative to each other with a fraction 65 , it is, of course, also possible to define $M_c$ in step 207 as $M_c$=(1−γ)·c·E·S1−ES2, where E is a number not equal to zero. E can be chosen, for instance, to be equal to $(1-\gamma)^{-1}$. In that case, only the signal S2 needs to be corrected with the fraction γ. In that case, it holds that $M_c$=cS1−(1−γ)S2 and therefore only the second measuring signal is corrected. E can also be selected to be equal to $(1-\gamma)^{1/2}$, so that $M_c$=$(1-\gamma)^{+\frac{1}{2}}$·cS−$(1-\gamma)^{-\frac{1}{2}}$·S2. Both are then subjected to a mutually different correction and are then corrected relative to each other.

With the above-described measuring procedure it has been found possible to reliably detect even minute blood spots in brown eggs. Surprisingly, it has been found that the fraction γ can be a substantially constant value which had good utility in brown eggs, regardless of their diameter, the thickness of the shell or the darkness of the shell, and that in all of these cases the above-defined corrected state parameter $M_c$ is a reliable indicator of the presence of blood.

It will be clear to one skilled in the art that the scope of protection of the present invention as defined by the claims is not limited to the embodiments represented in the drawings and discussed, but that it is possible to alter or modify the represented embodiments of the method according to the invention within the scope of the inventive concept. Thus it is possible, for instance, to skip step 207 and, instead of step 205, to compare the corrected measuring signal (1−γ)·c·S1 with S2.

Also, as stated, it is possible to compare a corrected signal S2 with S1. Moreover, a fraction γ' can be defined as γ'=1−γ. In the description given hereinabove and in the drawing, γ can then be replaced throughout with 1−γ'. The fraction γ' can then be determined in a brown-calibration according to the formula 1−γ'=$\Delta S$/S' (step 114). If the steps 112–114 are combined into a single step, γ' can be determined in a brown-calibration according to the formula 1−γ'=(c·S1−S2)/cS1. It follows that γ'=S2/cS1 in the brown-calibration. If γ' has thus been determined, the signals S1 and S2 can be corrected relative to each other with the fraction γ. This can be carried out, for instance, by multiplying the signal S1 by the fraction γ'. It is also possible to multiply the signal S2 by the fraction $(\gamma')^{-1}$. Naturally, it is also possible to multiply the signal S1 by E and the fraction γ' and to multiply the signal S2 by E, with E being a random number not equal to zero. In each of these cases, it holds that the signals S1 and S2 are corrected relative to each other with the fraction γ'. In step 207, $M_c$ can then be defined as $M_c$=cγ'·S1−S2, $M_c$=c·S1−$\gamma'^{-1}$·S2 or $M_c$=c·γ'·E·S1−E·S2, respectively. In the latter case, $M_c$ can optionally be defined in step 204 as $M_c$=c·E·S1−E·S2.

Figure 5:
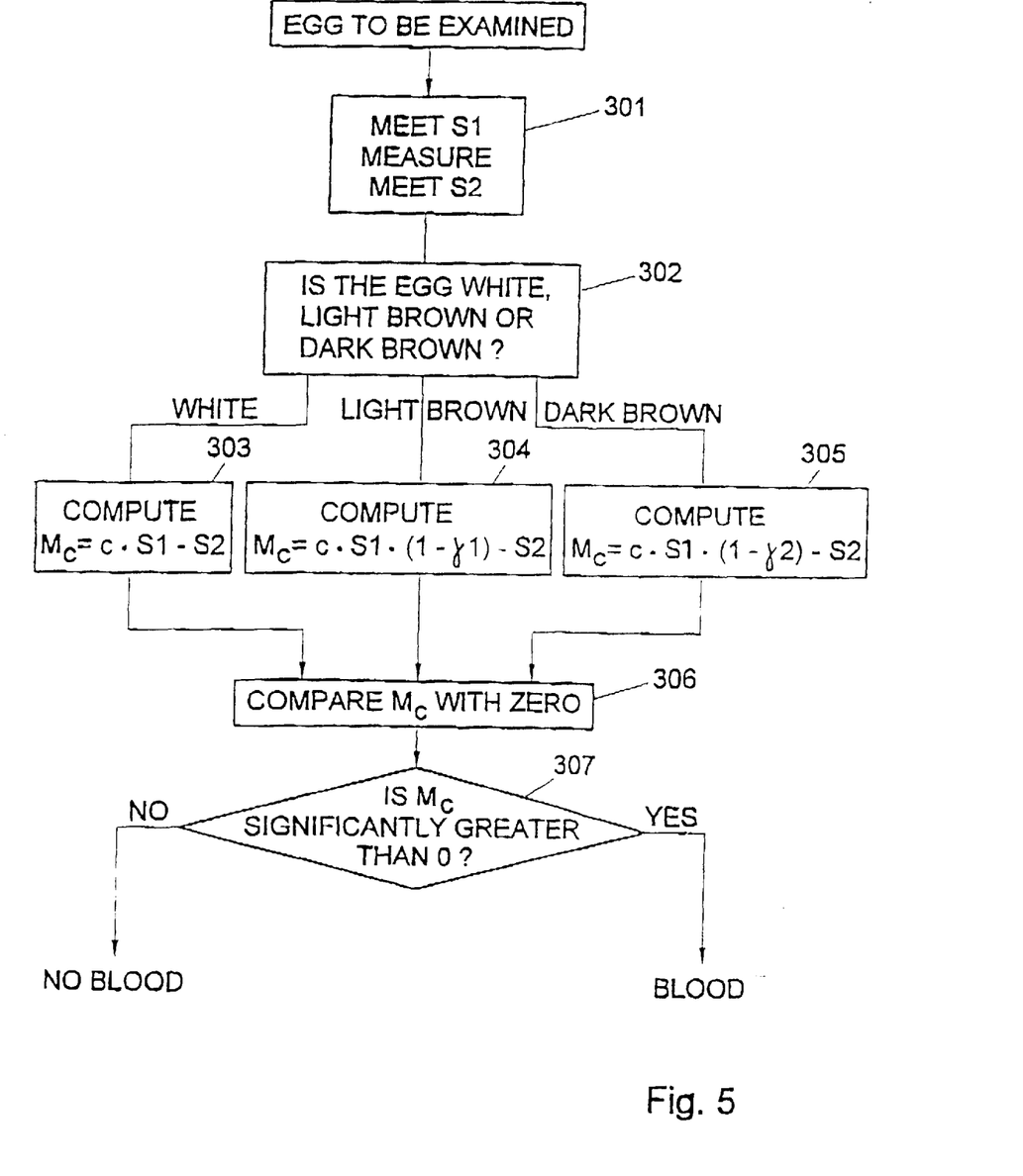
FIG. 5 is a flow diagram illustrating a second example of a measuring procedure according to the present invention.

In FIG. 5, a second example of a measuring method according to the invention is shown, which comprises a further refinement with respect to the method discussed with reference to FIG. 4. According to the method to be described with reference to FIG. 5, an egg with blood can be distinguished from an egg without blood with a further increased chance of success. The method also works well in, on the one hand, thick-shelled white versus thin-shelled brown eggs and, on the other hand, in light brown eggs and dark brown eggs. Again, in step 301 the first signal S1 and the second signal S2 are determined. Also, in a step 302 it is determined according to a predetermined criterion whether the egg under examination is a white egg, a light brown egg or a dark brown egg. In this example, the light brown eggs are separated from the dark brown eggs using a color camera, such as, for instance, two semiconductor diodes that are sensitive to green and red light, respectively. In this example, moreover, using the same camera, it is determined whether the egg is a white egg. Accordingly, in this example, using the camera, it is determined whether the egg is a white, a light brown or a dark brown egg.

If the egg is a white egg, a step 303 is carried out which is entirely analogous to the step 204. If the egg is a light brown egg, a step 304 is carried out which corresponds to step 207. The fraction γ1, however, is a fraction which has been determined in a light brown-calibration procedure for light brown eggs. All this is entirely analogous to the manner discussed for brown eggs with reference to FIG. 4. If the egg is a dark brown egg, a step 305 is carried out which is again equal to the step 207 discussed with reference to FIG. 4. In this case, however, a fraction γ2 is used for dark brown eggs, which has been obtained entirely analogously in a dark brown-calibration procedure for dark brown eggs, as has been discussed for brown eggs with reference to FIG. 4. Accordingly, the first and second measuring signal for light brown eggs are corrected relative to each other with a first fraction γ1 for light brown eggs, and the first and second measuring signal for dark brown eggs are corrected relative to each other with a second fraction γ2 for dark brown eggs. Accordingly, the fraction γ1 has been determined for light brown eggs in a light brown-calibration procedure on the basis of at least one bloodless light brown egg. Further, the fraction γ2 for dark brown eggs has been determined in a dark brown-calibration procedure on the basis of at least one bloodless dark brown egg. In addition, the first and second measuring signal for all eggs are corrected relative to each other with the first correction factor c, which has been determined in the white-calibration procedure on the basis of at least one bloodless white egg. Also, in step 304 for light brown eggs the second measuring signal S2 is compared with the first measuring signal corrected relative to the second measuring signal, (1−γ1)·c·S1, where c is the first correction factor satisfying c=S2/S1 in the case of a bloodless white egg. Here, the fraction γ1 for light brown eggs satisfies γ1=(c·S1−S2)/c·S1 in the case of a bloodless light brown egg. For dark brown eggs, it holds that the second measuring signal S2 is compared with the first measuring signal corrected relative to the second measuring signal, (1−γ2)·c·S1, where c is the above-mentioned first correction factor and where said fraction y2 for dark brown eggs satisfies γ2=(c·S1−S2)/c·S1 in the case of a bloodless dark brown egg. Again, in the white-calibration procedure a bloodless white egg is subjected to the radiation L1 and L2, the signals S1 and S2 are measured, and the first correction factor c is defined as c=S2/S1. Further, in the light brown-calibration procedure, a bloodless light brown egg is subjected to the radiation L1 and L2, the signals S1 and S2 are measured, and the fraction γ1 is determined according to the formula γ1=(c·S1−S2)/c·S1, and in the dark brown-calibration procedure a bloodless dark brown egg is subjected to the radiation L1 and L2, the signals S1 and S2 are measured, and the fraction γ2 is determined according to the formula γ2=(c·S1−S2)/c·S1.

When the value of $M_c$ in step 303, 304, or 305 has been determined, it is compared with 0. All this is carried out entirely analogously to the manner discussed for FIG. 4 with reference to step 205. Again, next, in step 307, entirely analogously to step 206 according to FIG. 4, it is determined whether the value of $M_c$ is significantly greater than 0. If this is the case, it is concluded that blood is present in the egg. If this is not the case, it is concluded that no blood is present in the egg.

It will be clear that steps 301 and 302 can be carried out in a random order. Further, it is possible to skip steps 303, 304 and 305 and instead, in step 306, to compare the corrected measuring signal cS1, cS1(1−γ1) or cS1(1−γ2) with S2. Also, again a fraction γ1' can be defined as γ1'=1−γ1 and a fraction γ2' can be defined as γ2'=1−γ2, all entirely analogously to the manner as discussed with reference to FIG. 4. Also, the signal S1 and the fractions γ1' and γ2' can then be multiplied again by the factor E mentioned earlier.

Such variants are each understood to fall within the scope of the invention.

What is claimed is:

1. A method for detecting the presence of undesired matter in an egg, comprising the steps of:
   (a) irradiating the egg to be examined with radiation which comprises at least two predetermined wavelength ranges;
   (b) providing a first measuring signal S1 representative of the amount of radiation in a first wavelength of said two predetermined wavelength ranges transmitted by the egg;
   (c) providing a second measuring signal S2 representative of the amount of radiation in a second wavelength of said two predetermined wavelength ranges by the egg;
   (d) automatically determining whether an egg to be examined is a white or brown egg;
   (e) only for brown eggs: correcting the first and second measuring signals relative to each other with at least one brown egg correction factor correcting for the shell being brown to produce corrected first and second measuring signals;
   (f) comparing the first measuring signal S1, with the second measuring signal S2 as corrected relative to each other in step (e); and.
   (g) determining the presence of undesired matter in the brown egg to be examined on the basis of the outcome of said comparison in step (f).

2. A method according to claim 1, characterized in that only for brown eggs, one of said two measuring signals is corrected with the at least one brown egg correction factor based on mathematical fraction of the first measuring signal S1.

3. A method according to claim 1, characterized in that the at least one brown egg correction factor is maintained constant for all brown eggs.

4. A method according to claim 1, characterized in that the at least one brown egg correction factor has been determined in a brown-calibration procedure based on at least one bloodless brown egg.

5. A method according to claim 4, wherein, in the brown-calibration procedure, a bloodless brown egg is subjected to the radiation, the signals S1 and S2 are measured, and the brown egg correction factor comprises γ determined according to the formula γ=(c·S1−S2)/c·S1, and where c is determined as c=S2/S1 and wherein S1 and S2 are determined in a white-calibration procedure wherein a bloodless white egg is subjected to the radiation and the signals S1 and S2 are measured.

6. A method according to claim 1, characterized in that the second measuring signal S2 is obtained in a wavelength range where blood has an absorption peak, and wherein the first measuring signal S1 is obtained at a wavelength which is located at a short distance next to said absorption peak.

7. A method according to claim 1, characterized in that further according to a predetermined criterion, light brown eggs are separated from dark brown eggs, while the first and second measuring signals for light brown eggs are corrected relative to each other with a light brown egg correction factor and the first and second measuring signals for dark brown eggs are corrected relative to each other with a dark brown egg correction factor, the light brown egg correction factor differing from the dark brown egg correction factor.

8. A method according to claim 7, characterized in that the light brown eggs are separated from dark brown eggs using a color-sensitive detector.

9. A method according to claim 8, characterized in that using the color-sensitive detector, it is determined whether an egg is a white, light brown or dark brown egg.

10. A method according to claim 7, characterized in that the light brown egg correction factor has been determined in a light brown-calibration procedure based on at least one bloodless light brown egg and the dark brown egg correction factor has been determined in a dark brown-calibration procedure based on at least one bloodless dark brown egg.

11. A method according to claim 10, characterized in that in the light brown-calibration procedure a bloodless light brown egg is subjected to the radiation, the signals S1 and S2 are measured, and the light brown egg correction factor comprises γ1 determined according to the formula γ1= (c·S1−S2)/c·S1, and in the dark brown-calibration procedure a bloodless dark brown egg is subjected to the radiation, the signals S1 and S2 are measured, and the dark brown egg correction factor comprises $\gamma 2$ determined according to the formula $\gamma 2=(c \cdot S1-S2)/c \cdot S1$, and where c is determined as $c=S2/S1$ and wherein S1 and S2 are determined in a white-calibration procedure wherein a bloodless white egg is subjected to the radiation and the signals S1 and S2 are measured.

12. A method according to claim 7, characterized in that for light brown eggs, the second measuring signal S2 is compared with a first measuring signal corrected relative to the second measuring signal, $(1-\gamma 1)\ c \cdot S1$, where c is a correction factor which satisfies $c=S2/S1$ in the case of a bloodless white egg, and $\gamma 1$ is the light brown egg correction factor having a value which satisfies $\gamma 1=(c \cdot S1-S2)/c \cdot S1$ in the case of a bloodless light brown egg; while for dark brown eggs, the second measuring signal S2 is compared with a first measuring signal corrected relative to the second measuring signal, $(1-\gamma 2)\ c \cdot S1$, where c is said correction factor and $\gamma 2$ is the dark brown egg correction factor having a value which satisfies $\gamma 2=(c \cdot S1-S2)/c \cdot S1$ in the case of a bloodless dark brown egg.

13. A method according to claim 1, characterized in that to determine whether an egg to be examined is a white or a brown egg, the first measuring signal S1 is compared with a white-reference.

14. A method according to claim 13, wherein, in a white-calibration procedure, a bloodless white egg is subjected to the radiation, the signals S1 and S2 are measured, and the white-reference is defined as the value of the first measuring signal S1.

15. A method according to claim 1, wherein the first and second measuring signal for all eggs are corrected relative to each other with a correction factor which has been determined in a white-calibration procedure based on at least one bloodless white egg.

16. A method according to claim 1, characterized in that the second measuring signal S2 is compared with a first measuring signal corrected relative to the second measuring signal, $(1-\gamma)\ c \cdot S1$, where C is a correction factor which satisfies $c=S2/S1$ in the case of a bloodless white egg, and $\gamma$ is the brown egg correction factor having a value which satisfies $\gamma=(c \cdot S1-S2)/c \cdot S1$ in the case of a bloodless brown egg.

17. A method according to claim 16, characterized in that in a white-calibrated procedure, a bloodless white egg is subjected to the radiation, the signals S1 and S2 are measured, and the correction factor c is determined as $c=S2/S1$.

18. A method according to claim 1, wherein the second wavelength is approximately equal to 577 nm and wherein the first wavelength is approximately equal to 597 nm.

19. A detection device for detecting the presence of undesirable matter in an egg, said method comprising:
at least one light source for irradiating the egg to be examined with radiation which comprises at least two predetermined wavelength ranges;
at least one detector for providing a first measuring signal S1 representative of the amount of radiation in a first wavelength of said two predetermined wavelength ranges transmitted by the eggs and for providing a second measuring signal S2 representative of the amount of radiation in a second wavelength of said two predetermined wavelength ranges transmitted by the eggs; and
a signal processing device of which a signal input is coupled for receiving said first and second measuring signals, wherein said signal processing device is arranged for:

comparing the first measuring signal with the second measuring signal for automatically determining the presence of undesired matter in the egg to be examined, regardless of egg color, on the basis of the outcome of said comparison,
wherein the detection device is adapted for automatically determining whether or not an egg is a brown egg and wherein the signal processing device is further adapted for correcting the first and second measuring signals relative to each other with at least one brown egg correction factor correcting for the shell being brown.

20. The device according to claim 10, further comprising a white-calibration procedure wherein the signal processing device is arranged to compute the correction factor c as $c=S2/S1$, wherein S1 and S2 are the signals from a white egg.

21. The device according to claim 19, further comprising a brown-calibration procedure wherein the signal processing device is arranged to determine the brown egg correction factor comprising $\gamma$ according to the formula $\gamma=(c \cdot S1-S2)/c \cdot S1$ wherein S1 and S2 are the signals from a brown egg and c is defined as $S2/S1$ wherein S1 and S2 are signals from a bloodless white egg.

22. The device according to claim 19, further comprising a light brown-calibration procedure wherein the signal processing device is arranged to determine a light brown egg correction factor comprising $\gamma 1$ according to the formula $\gamma 1=(c \cdot S1-S2)/c \cdot S1$ wherein S1 and S2 are signals for a light brown egg and c is a correction factor defined as $S2/S1$ where S1 and S2 are signals from a bloodless white egg, and a dark brown-calibration procedure to determine a dark egg correction factor comprising $\gamma 2$ according to the formula $\gamma 2=(c \cdot S1-S2)/c \cdot S1$ wherein S1 and S2 are signals from a dark brown egg, where c is a correction factor defined as $S2/S1$ wherein S1 and S2 are the signals from a bloodless white egg.

23. The device according to claim 19, wherein the signal processing device is arranged to determine in an actual measuring procedure whether an egg to be examined is a white, light brown or dark brown egg, and if the egg to be examined is a light brown egg, to compute the value $(1-\gamma 1) \cdot c \cdot S1$, and if the egg to be examined is a dark brown egg, to compute the value $(1-\gamma 2) \cdot c \cdot S1$, where c is a correction factor defined as $S2/S1$ wherein S1 and S2 are the signals from a bloodless white egg, $\gamma 1$ is a light brown egg correction factor and $\gamma 2$ is a dark brown egg correction factor.

24. A method for detecting the presence of undesired matter in an egg, comprising the steps of:
(a) irradiating the egg to be examined with radiation which comprises at least two predetermined wavelength ranges;
(b) providing a first measuring signal S1 representative of the amount of radiation in a first wavelength of said two predetermined wavelength ranges transmitted by the egg;
(c) providing a second measuring signal S2 representative of the amount of radiation in a second wavelength of said two predetermined wavelength ranges transmitted by the egg;
(d) automatically determining whether an egg to be examined is a white or brown egg;
(e) only for brown eggs:
(1) correcting the first and second measuring signals relative to each other with a calibration factor to provide corrected first and second measuring signals, and (2) correcting said corrected first and second measuring signals further with at least one brown egg correction factor to produce brown egg corrected first and second measuring signals;

(f) comparing the first signal S1 with the second measuring signal S2, as corrected relative to each other by (e)(1) or (e)(2); and (g) determining the presence of undesired matter in the brown egg to be examined on the basis of the outcome of said comparison in step (f).

25. A method for detecting the presence of undesired matter in an egg, comprising the steps of:

(a) irradiating the egg to be examined with radiation which comprises at least two predetermined wavelength ranges;

(b) providing a first measuring signal S1 representative of the amount of radiation in a first wavelength of said two predetermined wavelength ranges transmitted by the egg;

(c) providing a second measuring signal S2 representative of the amount of radiation in a second wavelength of said two predetermined wavelength ranges transmitted by the egg;

(d) automatically determining whether an egg to be examined is a white or brown egg;

(e) correcting the first and second measuring signals relative to each other for all eggs with a calibration factor;

(f) only for brown eggs: further correcting the corrected first and second measuring signals as corrected in step (e) relative to each other with at least a brown egg correction factor correcting to the egg shell being brown;

(g) comparing the corrected first and second measuring signals for white eggs as obtained in step (e) and comparing the corrected first and second measuring signals for brown eggs as obtained in step (f); and (h) determining the presence of undesired matter in the egg to be examined on the basis of said comparison in step (g).

26. A method for detecting the presence of undesired matter in an egg, comprising the steps of:

(a) irradiating the egg to be examined with radiation which comprises at least two predetermined wavelength ranges;

(b) providing a first measuring signal S1 representative of the amount of radiation in a first wavelength of said two predetermined wavelength ranges transmitted by the egg;

(c) providing a second measuring signal S2 representative of the amount of radiation in a second wavelength of said two predetermined wavelength ranges transmitted by the egg;

(d) automatically determining whether an egg to be examined is a white or brown egg;

(e) for white eggs: correcting the first and second measuring signals relative to each other with a first correcting factor to produce corrected first and second measuring signals;

(f) for brown eggs: correcting the first and second measuring signals relative to each other with at least one second correction factor which differs from the first correction factor to produce corrected first and second measuring signals;

(g) comparing the first and second measuring signal, S1,S2 as corrected in step (e) and (f), respectively; and (h) determining the presence of undesired matter in the egg to be examined on the basis of the outcome of said comparison in step (g).

* * * * *